United States Patent [19]

Urbach et al.

[11] Patent Number: 4,558,065
[45] Date of Patent: Dec. 10, 1985

[54] DERIVATIVES OF TRICYCLIC AMINOACIDS, PROCESSES FOR THEIR PREPARATION, AGENTS CONTAINING THESE COMPOUNDS AND THEIR USE, AND NEW BICYCLIC AMINOACIDS AS INTERMEDIATES AND PROCESSES FOR THEIR PREPARATION

[75] Inventors: Hansjörg Urbach, Kronberg; Rainer Henning, Frankfurt am Main; Reinhard Becker, Wiesbaden, all of Fed. Rep. of Germany

[73] Assignee: Hoechst Aktiengesellschaft, Fed. Rep. of Germany

[21] Appl. No.: 550,531

[22] Filed: Nov. 10, 1983

[30] Foreign Application Priority Data

Nov. 13, 1982 [DE] Fed. Rep. of Germany ....... 3242151

[51] Int. Cl.⁴ .................... A61K 37/00; C07C 103/52
[52] U.S. Cl. .................................. 514/412; 548/434; 260/112.5 R; 514/19
[58] Field of Search ................. 260/112.5 R; 548/434; 514/19, 12

[56] References Cited

U.S. PATENT DOCUMENTS 4,431,644  2/1984  Smith et al. .
4,431,645  2/1984  Smith et al. .

FOREIGN PATENT DOCUMENTS 0050800  5/1982  European Pat. Off. ..... 260/112.5 R
0088350  3/1983  European Pat. Off. .
3118191 11/1982  Fed. Rep. of Germany .
2491469  9/1982  France .

*Primary Examiner*—Delbert R. Phillips
*Attorney, Agent, or Firm*—Finnegan, Henderson, Farabow, Garrett & Dunner

[57] ABSTRACT

The invention relates to new derivatives of tricyclic aminoacids, of the formula I

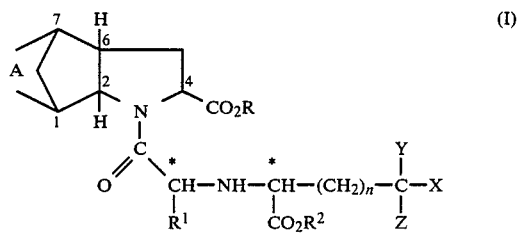

in which n denotes 0 or 1, A denotes —CH=CH— or —CH$_2$—CH$_2$—, R denotes hydrogen, alkyl or aralkyl, R$^1$ denotes hydrogen, or alkyl, which can optionally be substituted by amino, acylamino or benzoylamino, or alkenyl, cycloalkyl, cycloalkenyl, cycloalkylalkyl, aryl or partially hydrogenated aryl, each of which can be substituted by alkyl, alkoxy or halogen, or aralkyl or aroylalkyl, both of which can be substituted as defined above, or a monocyclic or bicyclic S-, O- and/or N-heterocyclene radical, or a side chain of a naturally occurring aminoacid, which may be protected, R$^2$ denotes hydrogen, alkyl, alkenyl or aralkyl, Y denotes hydrogen or hydroxyl and Z denotes hydrogen, or Y and Z together denote oxygen, and X denotes alkyl, alkenyl, cycloalkyl, aryl, which can be mono-, di- or tri-substituted by alkyl, alkoxy, hydroxyl, halogen, nitro, amino, alkylamino, dialkylamino and/or methylenedioxy, or 3-indolyl, and physiologically acceptable salts thereof, processes for their preparation, agents containing these compounds and their use, and new bicyclic aminoacids as intermediates and processes for their preparation.

10 Claims, No Drawings

DERIVATIVES OF TRICYCLIC AMINOACIDS, PROCESSES FOR THEIR PREPARATION, AGENTS CONTAINING THESE COMPOUNDS AND THEIR USE, AND NEW BICYCLIC AMINOACIDS AS INTERMEDIATES AND PROCESSES FOR THEIR PREPARATION

The invention relates to new derivatives of tricyclic aminoacids, of the formula I

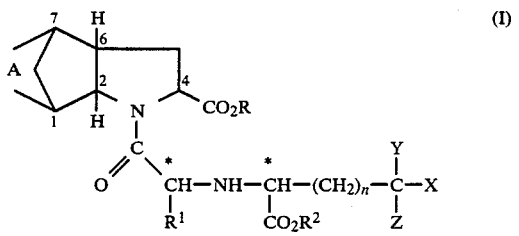

in which
n denotes 0 or 1,
A denotes —CH=CH— or —H$_2$—CH$_2$—,
R denotes hydrogen, ($C_1$ to $C_6$)-alkyl or aralkyl with 7 to 9 carbon atoms,
$R^1$ denotes hydrogen, or ($C_1$ to $C_6$)-alkyl, which can be optionally substituted by amino, ($C_1$ to $C_4$)-acylamino, in particular ($C_1$ to $C_4$)-alkanoyl amino, or benzoylamino, or ($C_2$ to $C_6$)-alkenyl, ($C_5$ to $C_9$)-cycloalkyl, ($C_5$ to $C_9$)-cycloalkenyl, ($C_5$ to $C_7$)-cycloalkyl-($C_1$ to $C_4$)-alkyl, ($C_6$ to $C_{12}$)-aryl or partially hydrogenated ($C_6$ to $C_{12}$)-aryl, each of which can be substituted by ($C_1$ to $C_4$)-alkyl, ($C_1$ or $C_2$)-alkoxy or halogen, or ($C_6$ to $C_{12}$)-aryl-($C_1$ to $C_4$)-alkyl or ($C_7$ to $C_{13}$)-aroyl-($C_1$ to $C_4$)-alkyl, both of which can be substituted in the aryl radical as defined above, or a monocyclic or bicyclic heterocyclene radical with 5 to 7 or 8 to 10 ring atoms, 1 or 2 ring atoms of which are sulfur or oxygen atoms and/or 1 to 4 ring atoms of which are nitrogen atoms, or a side chain of a naturally occurring aminoacid, which may be protected,
$R^2$ denotes hydrogen, ($C_1$ to $C_6$)-alkyl, ($C_2$ to $C_6$)-alkenyl or ($C_6$ to $C_{12}$)-aryl-($C_1$ to $C_4$)-alkyl,
Y denotes hydrogen or hydroxyl and
Z denotes hydrogen, or
Y and Z together denote oxygen, and
X denotes ($C_1$ to $C_6$)-alkyl, ($C_2$ to $C_6$)-alkenyl, ($C_5$ to $C_9$)-cycloalkyl, ($C_6$ to $C_{12}$)-aryl, which can be mono-, di- or tri-substituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkylamino and/or methylenedioxy, or 3-indolyl,
and physiologically acceptable salts thereof.

If $R^1$ represents a side chain of a protected naturally occurring α-aminoacid, such as, for example, protected Ser, Thr, Asp, Asn, Glu, Gln, Arg, Lys, Hyl, Cys, Orn, Cit, Tyr, Trp, His or Hyp, preferred protective groups are the conventional groups of peptide chemistry (cf. Houben-Weyl, Volume XV/1 and XV/2). If $R^1$ denotes the protected lysine side chain, the known amino-protective groups, especially ($C_1$-$C_6$)-alkanoyl, are preferred. Preferred O-protective groups for tyrosine are methyl and ethyl.

Possible salts are, in particular, alkali metal and alkaline earth metal salts, salts with physiologically acceptable amines and salts with inorganic or organic acids, such as, for example, HCl, HBr, H$_2$SO$_4$ maleic acid and fumaric acid.

Here and in the following text, aryl is to be understood as meaning preferably optionally substituted phenyl or naphthyl. This applies analogously to aroyl residues. Alkyl can be straight-chain or branched.

The configuration of the H atoms on C-2 and C-6 of the tricyclene is the cis configuration. There are also two other possible configurations of the H atoms on C-2 and C-6 of the tricyclic radical, i.e. the exoposition of the H atoms in respect of the bicyclic [2.2.1] part of the ring (radical Ia) and correspondingly the endo-position (radical Ib).

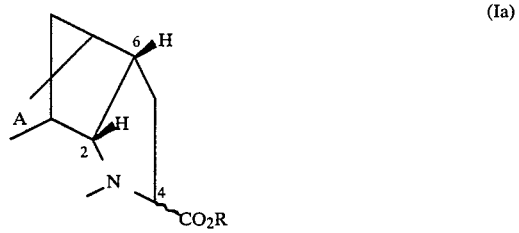

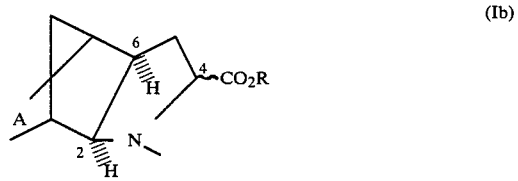

The carboxyl group on C-4 both in radical Ia and in radical Ib can be orientated in the trans-position (radicals Ic+If) or in the cis-position (radicals Id+Ie) relative to the hydrogen on C-2. This invention relates to all the abovementioned configuration isomers and the mirror image isomers of the formulae Ic to If.

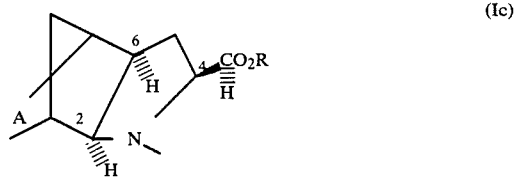

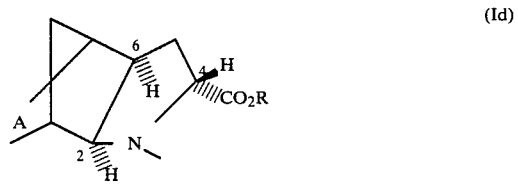

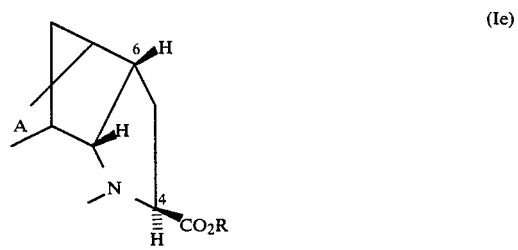

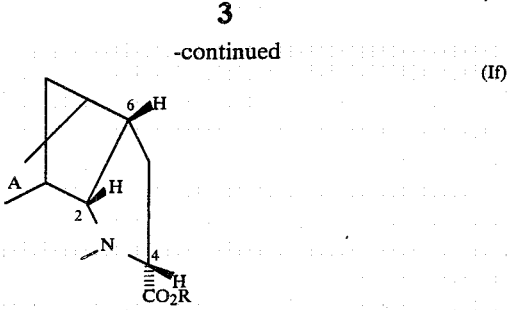

Compounds of the formula I have chiral carbon atoms in positions C-1, C-2, C-4, C-6 and C-7 and at the carbon atoms labeled with an asterisk in the side chain. The invention relates both to the R-configurations and to the S-configurations at all the centers. The compounds of the formula I can therefore be in the form of optical isomers, diastereomers, racemates or mixtures thereof. However, preferred compounds of the formula I are those in which C-4 in the tricyclic ring system and the carbon atoms labeled with an asterisk (*) in the side chain have the S-configuration, with the exception of (—CO—*CHR$^1$—NH—)=Cys, where the R-configuration is preferred.

Particularly preferred compounds of the formula I are those in which
n denotes 1,
A denotes CH=CH or CH$_2$—CH$_2$,
R denotes hydrogen or alkyl with 1 to 4 carbon atoms,
R$^1$ denotes hydrogen, (C$_1$ to C$_3$)-alkyl, (C$_2$ or C$_3$)-alkenyl, benzyl, 4-alkoxybenzyl, phenethyl, 4-aminobutyl or benzoylmethyl,
R$^2$ denotes hydrogen, (C$_1$ to C$_4$)-alkyl or benzyl and
X denotes phenyl, which can be mono- or di-substituted by (C$_1$ or C$_2$)-alkyl, (C$_1$ or C$_2$)-alkoxy, hydroxyl, fluorine, chlorine, bromine, amino, (C$_1$ to C$_4$)-alkylamino, di-(C$_1$ to C$_4$)-alkylamino, nitro and/or methylenedioxy or trisubstituted by methoxy,
and in particular those compounds of the formula I in which n denotes 1, A denotes CH$_2$-CH$_2$, R denotes hydrogen,
R$^1$ denotes methyl or the radical of an optionally protected naturally occurring aminoacid, X denotes phenyl, R$^2$ denotes hydrogen or ethyl, the hydrogen atoms on C-2 and C-6 have the cis-configuration and the exo- or endoconfiguration in respect of the bicyclic [2.2.1] skeleton, the carboxyl group on C-4 is orientated in the cis- or trans-position relative to the hydrogen on C-2, and the chiral carbon atoms labeled with an asterisk (*) and C-4 have the S-configuration.

Very particularly preferred compounds are endo-exo:
N-(1-S-carbethoxy-3-phenylpropyl)-S-alanyl-1R,2R, 4S, 6S, 7S-tricyclo [5.2.1.0$^{2.6}$]-3-aza-decane-4-carboxylic acid, N-(1-S-carboxy-3-phenylpropyl)-S-alanyl-1R, 2R, 4S, 6S, 7S-tricyclo [5.2.1.0$^{2.6}$]-3-aza-decane-4-carboxylic acid, N$_\alpha$-(1-S-carbethoxy-3-phenylpropyl)-S-lysyl-1R, 2R, 4S, 6S, 7S-tricyclo [5.2.1.0$^{2.6}$]-3-aza-decane-4-carboxylic acid and
N$_\alpha$-(1-S-carboxy-3-phenylpropyl)-S-lysyl-1R, 2R, 4S, 6S, 7S-tricylco [5.2.1.0$^{2.6}$]-3-aza-decane-4-carboxylic acid, endo-endo
N-(1-S-carbethoxy-3-phenylpropyl)-S-alanyl- 1S, 2S, 4S, 6R, 7R-tricyclo [5.2.1.0$^{2.6}$]-3-aza-decane-4-carboxylic acid, N-(1-S-carboxy-3-phenylpropyl)-3-alanyl-1S, 2S, 4S, 6R, 7R-tricyclo [5.2.1.0$^{2.6}$]-3-aza-decane-4-carboxylic acid, N$_\alpha$-(1-S-carbethoxy-3-phenylpropyl)-S-lysyl-1S, 2S, 4S, 6R, 7R-tricyclo [5.2.1.0$^{2.6}$]-3-aza-decane-4-carboxylic acid and N$_\alpha$-(1-S-carboxy-3-phenylpropyl)-S-lysyl-1S, 2S, 4S, 6R, 7R-tricyclo [5.2.1.0$^{2.6}$]-3-aza-decane-4-carboxylic acid, and exo-endo
N-(1-S-carbethoxy-3-phenylpropyl)-S-alanyl-1R, 2S, 4S, 6R, 7S-tricyclo [5.2.1.0$^{2.6}$]-3-aza-decane-4-carboxylic acid,
N-(1-S-carboxy-3-phenylpropyl)-S-alanyl-1R, 2S, 4S, 6R, 7S-tricyclo [5.2.1.0$^{2.6}$]-3-aza-decane-4-carboxylic acid, N$_\alpha$-(1-S-carbethoxy-3-phenylpropyl)-S-lysyl-1R, 2S, 4S, 6R, 7S-tricyclo [5.2.1.0$^{2.6}$]-3-aza-decane-4-carboxylic acid and
N$_\alpha$-(1-S-carboxy-3-phenylpropyl)-S-lysyl (1R, 2S, 4S, 6R, 7S-tricyclo [5.2.1.0$^{2.6}$]-3-aza-decane-4-carboxylic acid, and exo-exo
N-(1-S-carbethoxy-3-phenylpropyl)-S-alanyl-1S, 2R, 4S, 6S, 7R-tricyclo [5.2.1.0$^{2.6}$]-3-aza-decane-4-carboxylic acid,
N-(1-S-carboxy-3-phenylpropyl)-S-alanyl-1S, 2R, 4S, 6S, 7R-tricyclo [5.2.1.0$^{2.6}$]-3-aza-decane-4-carboxylic acid, N$_\alpha$-(1-S-carbethoxy-3-phenylpropyl)-S-lysyl-1S, 2R, 4S, 6S, 7R-tricyclo [5.2.1.0$^{2.6}$]-3-aza-decane-4-carboxylic acid and
N$_\alpha$-(1-S-carboxy-3-phenylpropyl)-S-lysyl-1S, 2R, 4S, 6S, 7R-tricyclo [5.2.1.0$^{2.6}$]-3-aza-decane-4-carboxylic acid.

The invention furthermore relates to processes for the preparation of the compounds of the formula I. One process varient comprises reacting a compound of the formula II

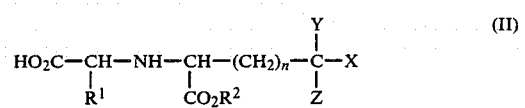

in which n, R$^1$, R$^2$, X, Y and Z have the meanings as in formula I, with a compound of the formula III

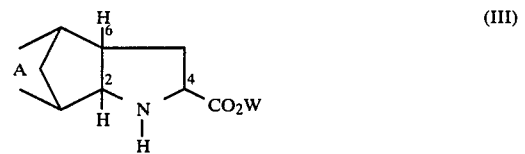

in which
A has the meaning as in formula I and
W denotes hydrogen or a radical which can be split off under acidic, basic or hydrogenolytic conditions, in particular a tert.-butyl or benzyl radical, by known amide formation methods of peptide chemistry, and, where relevant, subsequently splitting off the radical W by treatment with an acid or base or hydrogenolysis, and, where relevant, also splitting off the radical R$^2$ by additional treatment with acid or base, the free carboxylic acids in each case being obtained.

Further synthesis processes for the preparation of compounds of the formula I in which Y and Z together denote oxygen comprise reacting a compound of the formula IV

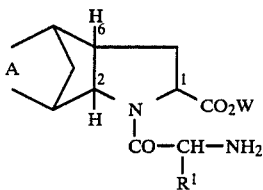 (IV)

in which $R^1$ and A have the meaning as in formula I and W has the meaning as in formula III, with a compound of the formula V $$R^2O_2C-CH=CH-CO-X \quad (V)$$

in which $R^2$ and X have the meanings as in formula I, in a Michael reaction in a known manner (Organikum, 6th edition, page 492, 1967), and, where relevant, splitting off the radical W and/or the radical $R^2$ as described above, or reacting a compound of the abovementioned formula IV with a compound of the general formula VI, in which $R^2$ has the meaning as in formula I, and with a compound of the general formula VII $$OHC-CO_2R^2 \quad (VI)$$

$$X-CO-CH_3 \quad (VII)$$

in which X has the meaning as in formula I, in a Mannich reaction in a known manner (Bull. Soc. Chim. France 1973, page 625), and, where relevant, subsequently splitting off the radical W and/or the radical $R^2$ as described above to form free carboxyl groups.

Compounds of the formula I in which Y and Z each denote hydrogen can also be prepared by reacting a compound of the abovementioned formula IV with a compound of the formula VIII

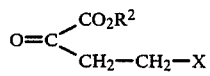 (VIII)

in which $R^2$ and X have the meanings as in formula I, by the procedure described in J. Amer. Chem. Soc. 93, 2897 (1971), reducing the resulting Schiff's bases and, where relevant, subsequently splitting off the radical W and/or the radical $R^2$ as described above to form the free carboxyl groups. The reduction of the Schiff's bases can be carried out catalytically, electrolytically or with reducing agents, such as, for example, complex boranates, preferably sodium borohydride or sodium cyanoborohydride.

Compounds of the formula I in which Y denotes hydroxyl and Z denotes hydrogen can also be obtained, for example, by reduction of a compound I in which Y and Z together denote oxygen obtained by the above procedures. This reduction can be carried out catalytically with hydrogen or with another reducing agent, such as sodium borohydride and other complex boranates or, for example, borane-amine complexes.

Compounds of the formula I in which R represents hydrogen can, if desired, be converted into their esters of the formula I in which R denotes ($C_1$ to $C_6$)-alkyl or ($C_7$-$C_9$)-aralkyl by methods which are known per se.

The invention also relates to compounds of the formula III in which the H atoms on C-2 and C-6 are in the cis-configuration relative to one another, the pyrrolidine ring is orientated in the endo- or exo-position relative to the bicyclic ring system, the group —$CO_2W$ on C-4 is in the cis- or trans-position relative to the hydrogen on C-2, W denotes hydrogen or a radical which can be split off under acid, basic or hydrogenolytic conditions and A denotes a CH=CH or $CH_2$—$CH_2$ group.

These compounds are used according to the invention as starting substances in the synthesis of compounds of the formula I, and be prepared, according to the invention, by the following procedure:

In one synthesis variant, a compound of the formula IX or X

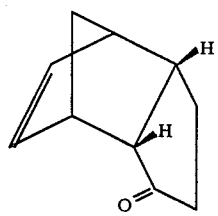 (IXa)

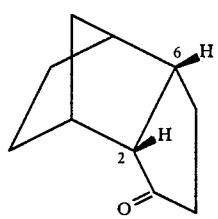 (IXb)

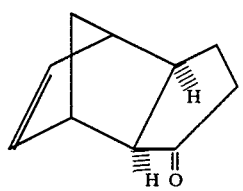 (Xa)

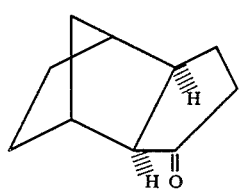 (Xb)

in which the hydrogen atoms on C-2 and C-6 are in the cis-configuration relative to one another and the cyclopentanone ring is orientated either in the endo-position (Formulae IX a and b) or in the exo-position (formulae X a and b) relative to the bicyclic ring systems, is used as the starting substances.

The compounds of the formula IX a and X a are known from R. R. Sauer, J. Org. Chem 39, 1850 (1974), and the compounds of the formula IX b and X b are described in J. Org. chem 32, 3120 (1967).

The ketones IX and X are converted by known methods into the oximes or oxime derivatives of the formula XI

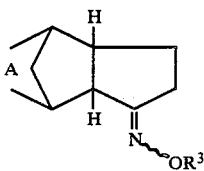

in which the H atoms on C-2 and C-6 are in the cis-configuration relative to one another, the cyclopentane ring is orientated in the endo- or exo-position relative to the bicyclic ring system, A denotes a CH=CH or CH$_2$—CH$_2$ group and R$^3$ denotes hydrogen, alkyl, aryl, aralkyl, —SO$_3$H, arylsulfonyl or another group suitable for Beckmann rearrangement. R$^3$ is preferably hydrogen, (C$_1$ to C$_6$)-alkyl, (C$_6$ to C$_9$)-aryl, (C$_7$ to C$_{10}$)-aralkyl, SO$_3$H, benzenesulfonyl or p-toluenesulfonyl. The compounds of the formula XI are converted into a compound of the formula XII

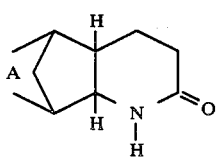

in which the H atoms on C-2 and C-7 are in the cis-configuration relative to one another, the lactam ring is orientated in the endo- or exo-position relative to the bicyclic ring system and A has the abovementioned meaning, in a Beckmann rearrangement, cf. Organic Reactions 11 (1960) 1-156, by reaction with a mineral acid, such as, for example, sulfuric acid or polyphosphoric acid, or, if R$^3$ denotes H, with benzenesulfonyl chloride or p-toluenesulfonyl chloride and a base, such as triethylamine, or with an organic acid, such as, for example, formic acid. The regio-isomers which arise after the Beckmann rearrangement can easily be removed by recrystallization or by column chromatography over silica gel. The compounds of the formula XII are halogenated to give a compound of the formula XIII

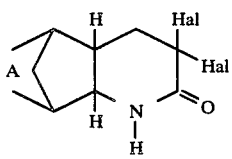

in which A has the abovementioned meaning and Hal denotes a halogen atom, preferably chlorine or bromine. Examples of suitable halogenating agents are inorganic acid halides, such as PCl$_5$, SO$_2$Cl$_2$, POCl$_3$, SOCl$_2$ and PBr$_3$, and halogens, such as bromine. It is advantageous to use PCl$_5$ or POCl$_3$ in combination with SO$_2$Cl$_2$. An imide halide is first formed as an intermediate, and then reacts further with the halogenating agents mentioned and by subsequent hydrolysis under basic conditions, preferably with aqueous alkali metal carbonate, to give a compound of the formula XIII.

The compounds of the formula XIII are subsequently catalytically reduced in a polar protic solvent, such as, for example, an alcohol, preferably ethanol, or a carboxylic acid, such as, for example, acetic acid, with addition of an acid acceptor, such as, for example, sodium acetate or triethylamine, to give a compound of the formula XIV

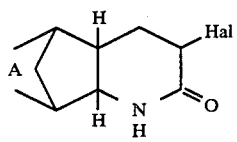

in which A and Hal have the abovementioned meanings. Examples of suitable catalysts are Raney nickel and palladium- or platinum-on-animal charcoal.

If A denotes CH=CH, it is necessary to protect the C-C double bonds via a cyclopentadienyl-iron dicarbonyl complex of the formula XV. The iron complex is removed again with Na in acetone after the hydrogenation, as described in J. Amer. Chem. Soc. 97, 3254 (1975) K. M. Nicholas.

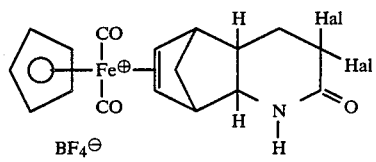

Compounds of the formula XIV can also be prepared directly by halogenation of the compounds of the formula XII using smaller amounts of the abovementioned halogenating agents.

Compounds of the formula XIV are converted into a compound of the formula III in which W denotes hydrogen by the known Favorskii reaction in the presence of a base, and, where relevant, the product is esterified. The abovementioned Favorskii reaction is carried out in an alcoholic solvent, such as methanol, ethanol or tert.-butanol, or in water or mixtures thereof at temperatures in the range from 20° C. to 140° C., preferably between 60° C. and 100° C. Alkali metal or alkaline earth metal hydroxides, such as sodium hydroxide, potassium hydroxide or barium hydroxide, or alkali metal alcoholates, such as, for example, sodium methylate or potassium tert.-butylate, are advantageously used as bases.

The compounds of the formula III in which W denotes hydrogen which are obtained by the Favorskii reaction are racemates, and can be obtained in the form of a diastereomer mixture. Thus, starting from the ketones of the formula IX, the aminoacids of the formulae IIIa and IIIb together with the mirror image isomers are obtained, and starting from the ketone of the formula X, the aminoacids of the formulae IIIc and IIId and the associated mirror image isomers are obtained, W denoting hydrogen and A having the above meaning.

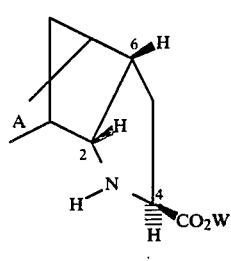

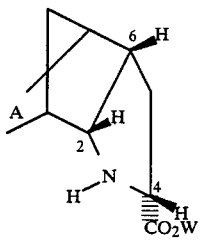
(IIIb)

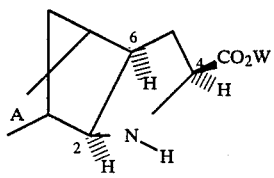
(IIIc)

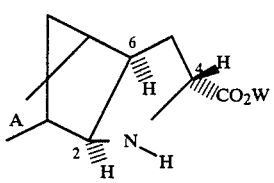
(IIId)

The hydrogen atoms on C-2 and C-6 are in the cis-configuration relative to one another in all four compounds of the formulae IIIa–IIId; in compounds of the formulae IIIa and IIIb, the pyrrolidine ring is orientated in the endo-position relative to the bicyclic ring system and in the formulae IIIc and IIId, the pyrrolidine ring is orientated in the exo-position, the —$CO_2W$ groups on C-4 in the compounds of the formulae IIIa and IIId are orientated in the cis-position relative to the hydrogen atom on C-2, and in the compounds of the formulae IIIb and IIIc these groups are correspondingly in the trans-position. In the following reactions, the corresponding racemates or diastereomer mixtures can be used. The racemates can also first be separated into the optical antipodes by known methods of peptide chemistry, and the diastereomer mixtures can be separated into the diastereomers by fractional crystallization, or by column chromatography over silica gel as diastereomers or after formation of suitable derivatives.

If desired, the aminoacids can be esterified. The preferred tert.-butyl esters and benzyl esters of the aminoacids of the formula III (W denotes tert.-butyl or benzyl) are obtained by the conventional methods of peptide chemistry, such as, for example, in the case of the tert.-butyl ester, by reaction of the acids with isobutylene in an inert organic solvent (for example dioxane) in the presence of acids (such as, for example, sulfuric acid). If A denotes CH=CH, the following process has proved to be particularly advantageous: the corresponding aminoacid is acylated on the nitrogen with a group which can be split off under basic conditions, such as, for example, the methylsulfonylethoxycarbonyl group (=MSC), Tesser, Balvert-Geers, Int. J. Pept. Protein Res. 7, 295 (1975).

The carboxylic acid is reacted with tert.-butanol in the neutral to weakly basic pH range in an organic solvent, such as, for example, pyridine, in the presence of propylphosphonic acid anhydride to give the corresponding tert.-butyl ester. The tert.-butyl ester of the formula III (W denotes, tert.-butyl) is obtained by splitting off the MSC protective group with an alkali in the strongly alkaline pH range in an aqueous solvent.

The benzyl esters of the formula II (W denotes benzyl) are obtained by the conventional method with benzyl alcohol and thionyl chloride.

The compounds of the formula II in which n denotes 1, Y and Z denote hydrogen, $R^1$ denotes methyl, $R^2$ denotes methyl or ethyl and X denotes phenyl which are used as starting substances for the preparation of compounds of the formula I are known (European Patent Application No. 37,231). The compounds of the formula II can be prepared by various procedures. In one synthesis variant, a ketone of the abovementioned formula VII is used as the starting substance, and is reacted with a compound of the abovementioned formula VI together with aminoacid esters of the formula XVI

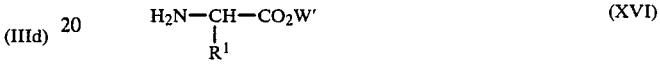
(XVI)

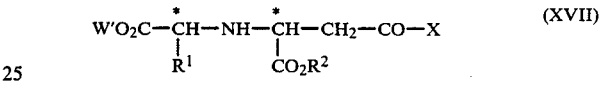
(XVII)

in which $R^1$ has the abovementioned meaning and $W'$ denotes a radical which can be eliminated by hydrogenolysis or under acidic conditions, in particular a benzyl or a tert.-butyl radical, by known procedures in a Mannich reaction to give a compound of the formula XVII in which $R^1$, $R^2$, X and $W'$ have the abovementioned meanings, with the restriction that if $W'$ denotes a radical which can be split off hydrogenolytically, in particular benzyl, $R^2$ may not have the meaning of $W'$. If the radical $W'$ is split off hydrogenolytically with the aid of, for example, palladium, compounds of the formula II in which Y and Z denote hydrogen are obtained with a hydrogen uptake of 3 molar equivalents. If the uptake of hydrogen is stopped at 1 molar equivalent, compounds of the formula II in which n denotes 1 and Y and Z together denote oxygen are obtained, these compounds also being obtained if the radical $W'$ of the formula XVII is split off with acids, such as, for example, trifluoroacetic acid or hydrochloric acid, in an inert organic solvent, such as, for example, dioxane.

Compounds of the formula XVII are also accessible by Michael additions of a compound of the abovementioned formula V to a compound of the abovementioned formula XVI by known procedures. This process is preferably suitable for the preparation of those compounds of the formula XVII in which $R^1$ denotes methyl, $R^2$ denotes ethyl and X denotes aryl.

The compounds of the formula XVII are obtained as diastereomer mixtures. Preferred diastereomers of the formula XVII are those in which the chiral carbon atoms labeled with an asterisk each have the S-configuration. These can be separated off by, for example, crystallization or chromatography, for example on silica gel. The configurations of the chiral carbon atoms are retained during subsequent splitting off of the radical $W'$.

The compounds of the abovementioned formula IV used as starting substances for the preparation of the compounds of the formula I are obtained from the compounds of the abovementioned formula III by reaction with an N-protected 2-aminocarboxylic acid of the formula XVIII

(XVIII)

in which V denotes a protective group and $R^1$ has the abovementioned meaning, by known procedures. Examples of suitable protective groups V which are split off again when the reaction has ended are tert.-butoxycarbonyl and benzyloxycarbonyl.

The reaction of a compound of the formula II with a compound of the formula III for the preparation of a compound of the formula I is carried out as a condensation reaction known in peptide chemistry, in which, for example, dicyclohexylcarbodiimide and 1-hydroxybenzotriazole are added as condensing agents. Trifluoroacetic acid or hydrochloric acid is preferably used as the acid in the subsequent splitting off of the radical W under acid conditions. The benzyl group (W denotes benzyl) is preferably split off by hydrogenolysis on palladium-on-charcoal in alcohol.

The configurations of the intermediates on the bridge head C-2 and C-6 are in each case retained in the reactions described above for the preparation of the compounds of the formulae III, IV and I.

The compounds of the formula III obtained according to the procedure described above are obtained as a mixture and can be separated from one another by, for example, recrystallization or chromatography.

The compounds of the formula III are obtained as racemic mixtures, and can be used as such in the other syntheses described above. However, after separation of the racemates into the optical antipodes by conventional methods, for example by salt formation with optically active bases or acids, they can also be used as pure enantiomers. The pure enantiomers can also be obtained.

If the compounds of the formula I are obtained as racemates, these can also be split into their enantiomers by the conventional methods, such as, for example, by salt formation with optically active bases or acids, or they can be separated by chromatography.

The compounds of the formula I according to the invention are in the form of inner salts if R is hydrogen. As amphoteric compounds, they can form salts with acids or bases. These salts are prepared in a conventional manner by reaction with one equivalent of acid or base.

The compounds of the formula I and their salts have a long-lasting, intensive hypotensive action. They are powerful inhibitors of the angiotensin-converting enzyme (ACE inhibitors). They can be used for combating high blood pressure of various origins. It is also possible to combine them with other hypotensive, vasodilating or diuretic compounds. Typical representatives of these classes of active compounds are described in, for example, Erhardt-Ruschig, Arzneimittel (Drugs), 2nd edition, Weinheim 1972. They can be used intravenously, subcutaneously or perorally.

The dosage for oral administration is 1–100 mg, preferably 1–40 mg, per individual dose for adult patients of normal weight, which corresponds to about 0.013–1.3 mg/kg/day, preferably 0.013 to 0.53 mg/kg/day. In severe cases, it can also be increased, since no toxic properties have as yet been observed. It is also possible to reduce the dose, and this is especially appropriate if diuretics are simultaneously administered.

The compounds according to the invention can be administered orally or parenterally in an appropriate pharmaceutical formulation. For an oral use form, the active compounds are mixed with the conventional additives for this, such as excipients, stabilizers or inert diluents, and are brought into suitable administration forms, such as tablets, dragees, push-fit capsules, aqueous, alcoholic or oily suspensions or aqueous, alcoholic or oily solutions, by conventional methods. Examples of inert carriers which can be used are gum arabic, magnesium carbonate, potassium phosphate, lactose, glucose and starch, especially maize starch. The formulation can be carried out either with dry granules or moist granules. Examples of suitable oily excipients or solvents are vegetable and animal oils, such as sunflower oil and cod-liver oil.

For subcutaneous or intravenous administration, the active compounds or physiologically acceptable salts thereof are dissolved, suspended or emulsified, if desired with the substances conventional for this, such as solubilizing agents, emulsifiers or other auxiliaries. Examples of suitable solvents for the new active compounds and the corresponding physiologically acceptable salts are: water, physiological saline solutions or alcohols, for example ethanol, propanediol and glycerol, and in addition also sugar solutions, such as glucose solutions or mannitol solutions, or a mixture of the various solvents mentioned.

The examples which follow serve to illustrate the invention, without restricting it to the compounds mentioned as representatives.

Unless indicated otherwise, the $^1$H-NMR data given in the examples which follow were determined by measurement in $CDCl_3$ and are given in δ (ppm).

EXAMPLE 1

N-(1-S-Carbethoxy-3-phenylpropyl)-S-alanyl-1R,2R,4S,6S,7S-tricyclo[5.2.1.0$^{2,6}$]-3-aza-decane-4-carboxylic acid hydrochloride.

(a) (±) Endo-tricyclo[6.2.1.0$^{2,7}$]-3-aza-4-oxo-undecane 7.8 g of (±) endo-tricyclo[5.2.1.0$^{2,6}$]-3-oxo-decane (Journ. Org. Chem. 32, 3120, 1967) are dissolved in 52 ml of 95% strength formic acid. 9.1 g of hydroxylamine-O-sulfonic acid, dissolved in 26 ml of 95% strength formic acid, are added dropwise thereto in the course of 10 minutes. The mixture is then boiled under reflux for 2 hours. After cooling, ice is added, and the mixture is neutralized with concentrated sodium hydroxide solution, with ice-cooling. The mixture is extracted with methylene chloride and the extract is washed with water, dried and concentrated on a rotary evaporator. Crude yield: 7.4 g of mixture. The mixture, which is composed of endo-tricyclo[6.2.1.0$^{2,7}$]-3-aza-4-oxo-undecane and endo-tricyclo[6.2.1.0$^{2,7}$]-4-aza-3-oxo-undecane is separated into its compounds over silica gel with methylene chloride/methanol 95:5.

Yield: 4.5 g; melting point: 170°–172° C.

(b) (±) Endo-tricyclo[6.2.1.0$^{2,7}$]-3-aza-4-oxo-5,5-dichloro-undecane 4.5 g of the lactam from Example 1a are dissolved in 70 ml of anhydrous chloroform, and 5.6 g of phosphorus pentachloride are added at room temperature, while stirring. 7.8 g of sulfuryl chloride in 8 ml of chloroform are added dropwise to this mixture in the course of 30 minutes, and the mixture is then refluxed for 3 hours. Thereafter, it is rendered neutral with saturated potassium carbonate solution, while cooling. After the chloroform phase has been separated off, the aqueous phase is extracted with methylene chloride and the organic phases are combined, washed with water, dried and concentrated in vacuo. The crude product is filtered over silica gel with methylene chloride/methanol 95:5.
Yield: 3.7 g; melting point: 199°–200° C.

(c) (±) Endo-tricyclo[6.2.1.0$^{2,7}$]-3-aza-4-oxo-5-chloroundecane.

2.9 g of the dichlorolactam from Example 1b and 1.7 ml of triethylamine are dissolved in 170 ml of ethanol. About 0.7 g of Raney nickel is added thereto and hydrogenation is carried out. After 1 equivalent of hydrogen has been taken up, the hydrogenation is interrupted, the catalyst is filtered off with suction and the ethanol solution is concentrated in vacuo. The residue is taken up in ethyl acetate and the mixture is washed with water, dried and evaporated. The residue is separated into its components over silica gel with methylene chloride/methanol 95:5.
Yield: 1.7 g; melting point: 179°–181° C.

(d) 1:1 mixture of 1R,2R,4S,6S,7S-tricyclo[5.2.1.0$^{2,6}$]-3-aza-decane-4-carboxylic acid and 1S,2S,4R,6R,7R-tricyclo[5.2.1.0$^{2,6}$]-3-aza-decane-4-carboxylic acid 1.3 g of the monochlorolactam from Example 1c are added to a boiling solution of 2.2 g of barium hydroxide octahydrate in 39 ml of water. The mixture is refluxed for 4 hours and then adjusted to pH 6.5 with concentrated sulfuric acid and refluxed for 1 hour. After cooling, the precipitate is filtered off with suction. The mother liquor is concentrated to dryness and the residue is crystallized from ethyl acetate.
Yield: 1.1 g; R$_f$ 0.61 (SiO$_2$; CH$_2$Cl$_2$/CH$_3$OH/CH$_3$CO$_2$H/H$_2$O 20:15:2:4)

According to the $^1$H-NMR (270 MHz), a small amount of 1S,2S,4S,6R,7R-tricyclo[5.2.1.0$^{2,6}$]-3-aza-decane-4-carboxylic acid and 1R,2R,4R,6S,7S-tricyclo[5.2.1.0$^{2,6}$]-3-aza-decane-4-carboxylic acid, which can be separated off, are formed.

(e) 1:1 mixture of benzyl 1R,2R,4S,6S,7S-tricyclo[5.2.1.0$^{2,6}$]-3-aza-decane-4-carboxylate hydrochloride and benzyl 1S,2S,4R,6R,7R-tricyclo[5.2.1.0$^{2,6}$]-3-aza-decane-4-carboxylate hydrochloride 10 ml of benzyl alcohol are cooled to −5° C. and 1.7 g of thionyl chloride are added dropwise. 1.1 g of the racemic aminoacid from Example 1d are added to this solution. The mixture is allowed to come to 0° C. and is stirred at 5° C. for 17 hours. The benzyl alcohol is distilled off in vacuo and the residue is triturated with diisopropyl ether.
Yield: 1.1 g.
$^1$H-NMR (DMSO-d$_6$): 1.0–3.0 (m, 5H), 3.2–4.8 (m 8H) 5.2 (s, 2H), 7.4 (broad s 5H) and 9.2–10.5 (broad, 2H).

(f) Benzyl N-(1-S-carbethoxy-3-phenylpropyl)-S-alanyl-1R,2R,4S,6S,7S-tricyclo-[5.2.1.0$^{2,6}$]-3-aza-decane-4-carboxylate 0.96 g of N-(1-S-carbethoxy-3-phenylpropyl)-S-alanine, 0.46 g of hydroxybenzotriazole, 1 g of the benzyl ester from Example 1e, 0.7 g of dicyclohexylcarbodiimide and 0.4 g of N-ethylmorpholine are added successively to 10 ml of anhydrous dimethylformamide, with ice-cooling, and the mixture is stirred at room temperature for 17 hours. It is then diluted with 12 ml of ethyl acetate and the urea which has precipitated is filtered off with suction. The solvent is distilled off in vacuo. The residue is taken up in ether and the mixture is washed with saturated sodium carbonate solution and water, dried and concentrated. The 1.7 g of residue is separated into the pure diastereomers over silica gel with cyclohexane/ethyl acetate 8:2.

The fraction which runs through rapidly contains benzyl N-(1-S-carbethoxy-3-phenylpropyl)-S-alanyl-1S,2S, 4R,6R,7R-tricyclo-[5.2.1.0$^{2,6}$]-3-aza-decane-4-carboxylate. 100 mg; m/e: 532; R$_f$=0.52 (SiO$_2$; cyclohexene/ethyl acetate 1:1).

The fraction which runs through slowly contains 400 mg of benzyl N-(1-S-carbethoxy-3-phenylpropyl)-S-alanyl-1R,2R,4S,6S,7S-tricyclo[5.2.1.0$^{2,6}$]-3-aza-decane-4-carboxylate.

m/e: 532; R$_f$=0.43 (SiO$_2$; cyclohexane/ethyl acetate 1:1).

(g) N-(1-S-Carbethoxy-3-phenylpropyl)-5-alanyl-1R,2R,4S,6S,7S-tricyclo[5.2.1.0$^{2,6}$]-3-aza-decane-4-carboxylic acid hydrochloride 350 mg of benzyl N-(1-S-carbethoxy-3-phenylpropyl)-S-alanyl-1R,2R,4S,6S,7S-tricyclo[5.2.1.0$^{2,6}$]-3-aza-decane-4-carboxylate from Example 1f are dissolved in 10 ml of ethanol, 30 mg of 10% strength palladium-on-charcoal are added and hydrogenation is carried out at room temperature. After the catalyst has been filtered off with suction, the solution is concentrated in vacuo, the residue is dissolved in ethyl acetate and the solution is rendered acid with ethanolic hydrogen chloride and concentrated on a rotary evaporator. The residue is triturated with diisopropyl ether.
Yield: 270 mg; melting point: 162°–165° C. (decomposition); R$_f$=0.42 (SiO$_2$; methylene chloride/methanol 8:2)

EXAMPLE 2

N-(1-S-Carbethoxy-3-phenylpropyl)-S-alanyl-1S,2S,4S,6R,7R-tricyclo[5.2.1.0$^{2,6}$]-3-aza-decane-4-carboxylic acid hydrochloride N-(1-S-Carbethoxy-3-phenylpropyl)-S-alanyl-1S,2S,4S,6R,7R-tricyclo[5.2.1.0$^{2,6}$]-3-aza-decane-4-carboxylic acid hydrochloride is obtained in an analogous manner by the process described in Example 1e to 1g using 1S,2S,4S,6R,7R-tricyclo[5.2.1.0$^{2,6}$]-3-aza-decane-4-carboxylic acid as the starting substance.

EXAMPLE 3

N-(1-S-Carbethoxy-3-phenylpropyl)-S-alanyl-1S,2R,4S,6S,7R-tricyclo[5.2.1.0$^{2,6}$]-3-aza-decane-4-carboxylic acid (a) (±) Exo-tricyclo[6.2.1.0$^{2,7}$]-3-aza-4-oxo-undecane The compound is prepared by the process described in Example 1(a), starting from (±) exo-tricyclo[5.2.1.0$^{2,6}$]-3-oxo-decane (Journ. Org. Chem. 32, 3120 (1967)). The lactam mixture is separated into its components over silica gel using methylene chloride/methanol 9:1. R$_f$=0.49 (SiO$_2$; CH$_2$Cl$_2$/CH$_3$OH 9:1); melting point: 178°–180° C.

(b) (±) Exo-tricyclo[6.2.1.0$^{2,7}$]-3-aza-4-oxo-5,5-dichloroundecane

The compound is prepared by the process described in Example 1b, starting from the lactam of Example 3a. Melting point: 240° C.; R$_f$:0.49 (SiO$_2$; CH$_2$Cl$_2$/CH$_3$OH 95:5)

(c) (±) Exo-tricyclo[6.2.1.0$^{2,7}$]-3-aza-4-oxo-5-chloroundecane.

The compound is prepared by the process described in Example 1c, starting from the dichlorolactam of Example 3b.
R$_f$=0.26 (SiO$_2$; CH$_2$Cl$_2$/CH$_3$OH 95:5).

(d) 1:1 mixture of 1S,2R,4S,6S,7R-tricyclo[5.2.1.0^{2.6}]-3-aza-decane-4-carboxylic acid and mirror image isomers and 1R,2S,4S,6R,7S-tricyclo[5.2.1.0^{2.6}]-3-aza-decane-4-carboxylic acid and mirror image isomers The compounds are prepared by the process described in Example 1d, starting from the monochlorolactam of Example 3c.

$R_f$=0.54 (SiO$_2$; CH$_2$Cl$_2$/CH$_3$OH/CH$_3$CO$_2$H/H$_2$O 20:15:2:4). NMR (D$_2$O): 0.9–1.6 (m 8H); 2.1–2.5 (m 3H); and 3.4–4.0 (m, 2H).

(e) 1:1 mixture of benzyl 1S,2R,4S,6S,7R-tricyclo[5.2.1.0^{2.6}]-3-aza-decane-4-carboxylate and mirror image isomers and benzyl 1R,2S,4S,6R,7S-tricyclo[5.2.1.0^{2.6}]-3-aza-decane-4-carboxylate and mirror image isomers The compounds are prepared by the process described in Example 1e, starting from the aminoacid mixture of Example 3d.

$R_f$=0.31, diastereomer I (SiO$_2$; CH$_2$Cl$_2$/CH$_3$OH 95:5). $R_f$=0.26 diastereomer II.

The mixture can be separated preparatively into the two racemic diastereomers chromatographically over silica gel after N-acylation.

(f) Mixture of benzyl N-(1-S-carbethoxy-3-phenylpropyl)-S-alanyl-1S,2R,4S,6S,7R-tricyclo[5.2.1.0^{2.6}]-3-aza-decane-4-carboxylate, benzyl N-(1-S-carbethoxy-3-phenylpropyl)-S-alanyl-1R,2S,4R,6R,7S-tricyclo[5.2.1.0^{2.6}]-3-aza-decane-4-carboxylate, benzyl N-(1-S-carbethoxy-3-phenylpropyl)-S-alanyl-1R,2S,4S,6R,7S-tricyclo-[5.2.1.0^{2.6}]-3-aza-decane-4-carboxylate and benzyl N-(1-S-carbethoxy-3-phenylpropyl)-S-alanyl-1S,2R,4R,6S,7R-tricyclo[5.2.1.0^{2.6}]-3-aza-decane-4-carboxylate The compounds are prepared by the process described in Example 1f, starting from the benzyl ester mixture of Example 3e. The diastereomer mixture is separated into its components over silica gel using methylene chloride/ethyl acetate 99:1 to 8:2.

Diastereomer A $R_f$=0.134 (SiO$_2$; methylene chloride/ethyl acetate 95:5). m/e=532.

Diastereomer B $R_f$=0.126 (SiO$_2$; methylene chloride/ethyl acetate 95:5). m/e=532.

Diastereomer C $R_f$=0.105 (SiO$_2$; methylene chloride/ethyl acetate 95:5). m/e=532.

Diastereomer D $R_f$=0.074 (SiO$_2$; methylene chloride/ethyl acetate 95:5). m/e=532.

(g) N-(1-S-Carbethoxy-3-phenylpropyl)-S-alanyl-1S,2R,4S,6S,7R-tricyclo[5.2.1.0^{2.6}]-3-aza-decane-4-carboxylic acid hydrochloride, N-(1-S-carbethoxy-3-phenylpropyl)-S-alanyl-1R,2S,4R,6R,7S-tricyclo[5.2.1.0^{2.6}]-3-aza-decane-4-carboxylic acid hydrochloride, N-(1-S-carbethoxy-3-phenylpropyl)-S-alanyl-1R,2S,4S,6R,7S-tricyclo[5.2.1.0^{2.6}]-3-aza-decane-4-carboxylic acid hydrochloride and N-(1-S-carbethoxy-3-phenylpropyl)-S-alanyl-1S,2R,4R,6S,7R-tricyclo[5.2.1.0^{2.6}]-3-aza-decane-4-carboxylic acid hydrochloride are formed when the diastereomers A, B, C and D of Example 3g are each reacted by the process described in Example 1g.

Diastereomer A'

$R_f$=0.191 (SiO$_2$; methylene chloride/methanol 9:1). m/e: 514 as the trimethylsilyl derivative.

Diastereomer B'

$R_f$=0.231 (SiO$_2$; methylene chloride/methanol 9:1). m/e: 514 as the trimethylsilyl derivative.

diastereomer C'

$R_f$=0.301 (SiO$_2$; methylene chloride/methanol 9:1). m/e: 514 as the trimethylsilyl derivative.

Diastereomer D'

$R_f$=0.358 (SiO$_2$; methylene chloride/methanol 9:1). m/e: 514 as the trimethylsilyl derivative.

EXAMPLE 4

N-(1-S-Carboxy-3-phenylpropyl)-S-alanyl-1R,2R,4S,6S,7S-tricyclo[5.2.1.0^{2.6}]-3-aza-decane-4-carboxylic acid 1 g of the ester from Example 1g is dissolved in 20 ml of dimethoxyethane. One drop of a dilute indicator solution, for example bromothymol blue, is added, and an equivalent amount of 4N aqueous potassium hydroxide solution is added in the course of 5 minutes, with vigorous stirring, so that the indicator shows a pH value of 9–10 at the end of the reaction. The mixture is then adjusted to pH 4 with hydrochloric acid and concentrated to dryness in vacuo, the residue is taken up in ethyl acetate and the mixture is filtered. After the ethyl acetate solution has been concentrated, 0.75 g of a solid residue is obtained.

m/e: 414.

EXAMPLE 5

N-(1-S-Carboxy-3-phenylpropyl)-S-alanyl-1S,2R,4S,6S,7R-tricyclo[5.2.1.0^{2.6}]-3-aza-decane-4-carboxylic acid, N-(1-S-carboxy-3-phenylpropyl)-S-alanyl-1R,2S,4R,6R,7S-tricyclo[5.2.1.0^{2.6}]-3-aza-decane-4-carboxylic acid, N-(1-S-carboxy-3-phenylpropyl)-S-alanyl-1R,2S,4S,6R,7S-tricyclo[5.2.1.0^{2.6}]-3-aza-decane-4-carboxylic acid and N-(1-S-carboxy-3-phenylpropyl)-S-alanyl-1S,2R,4R,6S,7R-tricyclo[5.2.1.0^{2.6}]-3-aza-decane-4-carboxylic acid are formed from the diastereomers A', B', C' and D' of Example 3g after hydrolysis, as described in Example 4.

EXAMPLE 6

N-(1-S-Carbethoxy-3-oxo-3-phenylpropyl)-S-alanine benzyl ester 65.7 g of ethyl 4-phenyl-4-oxo-butene-2-carboxylate (ethyl benzoylacrylate) are dissolved in 225 ml of ethanol, and 1 ml of triethylamine is added. A solution of 70 g of S-alanine benzyl ester in 90 ml of ethanol is rapidly added dropwise to this solution at room temperature. The mixture is stirred at room temperature for 2 hours and the solution is then cooled. The S,S-isomer crystallizes out.

Yield: 94.3 g; melting point: 73°–74° C.

$[\alpha]_D^{20}$=+17.8° (c=1, CH$_3$OH).

EXAMPLE 7

N-(1-S-Carbethoxy-3-oxo-3-phenylpropyl)-S-alanine 0.5 g of the compound from Example 6 are dissolved in 40 ml of ethanol, 0.1 g of 10% strength Pd/C is added and hydrogenation is carried out at room temperature and under normal pressure.

Yield: 300 mg; melting point: 210°–220° C. $^1$H-NMR (DMSO-$d_6$): 1.0–1.4 (t, 6H); 3.2–5.0 (m, 8H); 7.2–8.1 (m, 5H).

EXAMPLE 8

Benzyl N-(1-S-carbethoxy-3-oxo-3-phenylpropyl)-S-alanyl-1R,2R,4S,6S,7S-tricyclo[5.2.1.0$^{2.6}$]-3-aza-decane-4-carboxylate The compound is prepared analogously to the process described in Example 1f from the benzyl ester mixture of Example 1e and N-(1-S-carbethoxy-3-oxo-3-phenyl-propyl-S-alanine from Example 7. The diastereomers are separated over silica gel.

EXAMPLE 9

N-(1-S-Carbethoxy-3-oxo-3-phenylpropyl)-S-alanyl-1R,2R,4S,6S,7S-tricyclo[5.2.1.0$^{2.6}$]-3-aza-decane-4-carboxylic acid 1 g of the benzyl ester from Example 8 is dissolved in 30 ml of ethanol and hydrogenation is carried out with 100 mg of Pd/C (10% strength) at room temperature and under normal pressure. After one molar equivalent of hydrogen has been taken up, the hydrogenation is interrupted. The catalyst is filtered off with suction and the solution is concentrated.

Yield: 750 mg of an oil.

The following compounds are prepared analogously by the process described in Examples 8 and 9, starting from the aminoacid benzyl esters of Example 3e: N-(1-S-carbethoxy-3-oxo-3-phenylpropyl)-S-alanyl-1S,2R,4S,6S,7R- tricyclo[5.2.1.0$^{2.6}$]-3-aza-decane-4-carboxylic acid, N-(1-S-carbethoxy-3-oxo-3-phenylpropyl)-S-alanyl-1R,2S,4R,6R,7S-tricyclo[5.2.1.0$^{2.6}$]-3-aza-decane-4-carboxylic acid, N-(1-S-carbethoxy-3-oxo-3-phenylpropyl)-S-alanyl-1R,2S,4S,6R,7S-tricyclo[5.2.1.0$^{2.6}$]-3-aza-decane-4-carboxylic acid and N-(1-S-carbethoxy-3-oxo-phenylpropyl)-S-alanyl-1S,2R,4R,6S,7R-tricyclo[5.2.1.0$^{2.6}$]-3-aza-decane-4-carboxylic acid.

EXAMPLE 10

$N_\alpha$-(1-S-Carbethoxy-3-phenylpropyl)-S-lysyl-1R,2R,4S,6S,7S-tricyclo[5.2.1.0$^{2.6}$]-3-aza-decane-4-carboxylic acid dihydrochloride (a) $N_\alpha$-(1-S-Carbethoxy-3-oxo-3-phenylpropyl)-$N_\epsilon$-benzyloxycarbonyl-S-lysine benzyl ester.

10 g of ethyl 4-phenyl-4-oxo-butene-2-carboxylate are dissolved in 100 ml of ethanol. 19.1 g of $N_\epsilon$-benzyloxycarbonyl-S-lysine benzyl ester and 0.2 g of triethylamine are added thereto. The solution is stirred at room temperature for 3 hours and is then concentrated in vacuo. The oily residue (31 g) is dissolved in isopropanol/diisopropyl ether and the solution is cooled. 13 g of $N_\alpha$-(1-S-carbethoxy-3-oxo-3-phenylpropyl)-$N_\epsilon$-benzyloxycarbonyl-S-lysine benzyl ester crystallize.

$\alpha_D^{20}$ = 3.5° (c=1, CH$_3$OH). $^1$H-NMR (CDCl$_3$): 1.0–1.4 (tr. 3H); 1.0–2.0 (m, 9H); 2.0–2.6 (broad s, 1H); 2.9–3.9 (m, 6H); 3.9–4.4 (Q, 2H); 4.6–4.9 (broad s, 1H); 5.0–5.2 (double s, 4H) 7.1–8.1 (m, 15H).

(b) $N_\alpha$-(1-S-Carbethoxy-3-phenylpropyl)-$N_\epsilon$-benzyloxycarbonyl-S-lysine.

4.0 g of the lysine benzyl ester derivative prepared in Example 10a are dissolved in 50 ml of glacial acetic acid, and 0.6 g of Pd/C (10% strength) and 0.6 g of concentrated sulfuric acid are added thereto. Hydrogenation is carried out at room temperature and under normal pressure for 6 hours. The catalyst is then filtered off with suction and the ethanolic solution is stirred with 1.4 g of solid sodium bicarbonate. The solution is concentrated on a rotary evaporator and the residue is dissolved in water. The aqueous phase is extracted with ethyl acetate and methylene chloride. The organic phases are discarded and the aqueous phase is evaporated to dryness in vacuo. The residue is extracted by stirring with methanol. After the methanol has been evaporated off, an oily residue remains, which solidifies when treated with diisopropyl ether. Yield of $N_\alpha$-(1-S-carbethoxy-3-phenylpropyl)-S-lysine: 2.0 g.

$^1$H-NMR (D$_2$O): 1.0–1.4 (tr, 3H); 1.0–2.5 (m, 9H), 2.5–4.4 (m, 9H); 3.9–4.4 (q, 2H), 4.5–5.0 (m, 1H); 7.1–7.6 (m, 5H) m/e: 336.

3.4 g of $N_\alpha$-(1-S-carbethoxy-3-phenylpropyl)-S-lysine are dissolved in 30 ml of methylene chloride and the solution is cooled to 0° C. With ice-cooling, 2.1 g of triethylamine are added thereto, and 1.9 g of benzyl chloroformate are then added dropwise. The mixture is stirred at 0° C. for 1 hour and then brought to room temperature. The methylene chloride solution is then extracted by shaking with water, sodium carbonate solution and water. After drying, the solution is concentrated and the oily residue is chromatographed over silica gel using methylene chloride/methanol. 2.0 g of $N_{60}$ -(1-S-carbethoxy-3-phenylpropyl)-$N_\epsilon$-benzyloxycarbonyl-S-lysine are obtained.

$^1$H-NMR (D$_2$O): 1.0–1.4 (tr, 3H); 1.0–2.5 (m,9H); 2.5–4.4 (m, 9H); 3.9–4.4 (q, 2H); 4.5–5.0 (m, 1H); 5.1 (s, 2H); 7.1–7.5 (m, 10H).

(c) Benzyl $N_\alpha$-(1-S-carbethoxy-3-phenylpropyl)-$N_\epsilon$-benzyloxycarbonyl-S-lysyl-1R,2R,4S,6S,7S-tricyclo[5.2.1.0$^{2.6}$]-3-aza-decane-4-carboxylate 500 mg of the benzyl ester hydrochloride prepared in Example 1E are reacted with 900 mg of $N_\alpha$-(1-S-carbethoxy-3-phenylpropyl)-$N_\epsilon$-benzyloxycarbonyl-S-lysine, prepared according to Example 10b, analogously to Example 1F. After working up, 1.5 g of an oil which is a mixture of two diastereomeric compounds are obtained.

The diastereomeric mixture is separated into the individual components by column chromatography with silica gel, and cyclohexane/ethyl acetate 2:1 as the eluting agent. The isomer eluted first is the above compound. 0.6 g of oil is obtained.

$^1$H-NMR (CDCl$_3$, after replacement of H by D with D$_2$O): 0.9–3.1 (m, 18H); 3.2–5.1 (m, 14H), 5.1–5.3 (ds, 4H) 7.1–7.6 (m, 15H).

(d) $N_\alpha$-(1-S-Carbethoxy-3-phenylpropyl)-S-lysyl-1R,2R,4S,6S,7S-tricyclo[5.2.1.0$^{2.6}$]-3-aza-decane-4-carboxylic acid dihydrochloride 500 mg of benzyl $N_\alpha$-(1-S-carbethoxy-3-phenylpropyl)-$N_\epsilon$-benzyloxycarbonyl-S-lysyl-1R,2R,4S,6S,7S-tricyclo[5.2.1.0$^{2.6}$]-3-aza-decane-4-carboxylic acid benzyl ester from Example 10c are dissolved in 20 ml of ethanol and hydrogenolytic debenzylation is carried out under normal pressure, with addition of 0.1 g of 10% strength Pd/C. When the uptake of hydrogen has ended, the catalyst is filtered off, ethanolic hydrogen chloride solution is added to the ethanolic solution until the pH reaches 1, and the ethanol is evaporated off in vacuo. Diisopropyl ether is added to the residue, whereupon the product solidifies. 200 mg are obtained.

NMR (D$_2$O): 1.0–3.1 (m, 18H); 3.1–5.2 (m, 14H) 7.2 (s, 5H).

EXAMPLE 11

The following compounds are obtained analogously by the process described in Example 10c, by reacting the aminoacid benzyl ester of Example 3e with N$_\alpha$-(1-S-carbethoxy-3-phenylpropyl)-N-benzyloxycarbonyl-S-lysine, described in Example 10b: benzyl N$_\alpha$-(1-S-carbethoxy-3-phenylpropyl)-N$_\epsilon$-benzyloxycarbonyl-S-lysyl-1S,2R,4S,6S,7R-tricyclo[5.2.1.0$^{2.6}$]-3-aza-decane-4-carboxylate (Diastereomer E), benzyl N$_\epsilon$-(1-S-carbethoxy-3-phenylpropyl)-N$_\epsilon$-benzyloxycarbonyl-S-lysyl-1R,2S,4R,6R,7S-tricyclo[5.2.1.0$^{2.6}$]-3-aza-decane-4-carboxylate (Diastereomer F), benzyl N$_\epsilon$-(1-S-carbethoxy-3-phenylpropyl)-N$_{6S}$-benzyloxycarbonyl-S-lysyl-1R,2S,4S,6R,7S-tricyclo-[5.2.1.0$^{2.6}$]-3-aza-decane-4-carboxylate (Diastereomer G) and benzyl N$_\epsilon$-(1-S-carbethoxy-3-phenylpropyl)-N$_\epsilon$-benzyloxycarbonyl-S-lysyl-1S,2R,4R,6S,7R-tricyclo[5.2.1.0$^{2.6}$]-3-aza-decane-4-carboxylate (Diastereomer H).

If the benzyl 1S,2S,4S,6R,7R-tricyclo[5.2.1.0$^{2.6}$]-3-aza-decane-4-carboxylate is used, benzyl N$_\epsilon$-(1-S-carbethoxy-3-phenylpropyl)-N$_\epsilon$-benzyloxycarbonyl-S-lysyl-1S,2S,4S,6R,7R-tricyclo[5.2.1.0$^{2.6}$]-3-aza-decane-4-carboxylate (Diastereomer K) is obtained analogously.

EXAMPLE 12

If the diastereomers E, F, G, H and K are hydrogenated by the process described in Example 10d, diastereomer E gives N$_\alpha$-(1-S-carbethoxy-3-phenylpropyl)-S-lysyl-1S,2R,4S,6S,7R-tricyclo[5.2.1.0$^{2.6}$]-3-aza-decane-4-carboxylic acid dihydrochloride (Diastereomer E′)

$^1$H-NMR (D$_2$O): 0.9–3.0 (m, 18H), 3.0–4.9 (m, 14H), 7.2 (s, 5H), diastereomer F gives N$_\alpha$-(1-S-carbethoxy-3-phenylpropyl)-S-lysyl-1R,2S,4R,6R,7S-tricyclo[5.2.1.0$^{2.6}$]-3-aza-decane-4-carboxylic acid dihydrochloride (diastereomer F′)

$^1$H-NMR (D$_2$O): 1.0–3.2 (m 18H); 3.2–5.1 (m, 14H); 7.1 (s, 5H), diastereomer G gives N$_\alpha$-(1-S-carbethoxy-3-phenylpropyl)-S-lysyl-1R,2S,4S,6R,7S-tricyclo[5.2.1.0$^{2.6}$]-3-aza-decane-4-carboxylic acid dihydrochloride (diastereomer G′)

$^1$H-NMR (D$_2$O): 1.0–3.3 (m, 20H); 3.4–5.0 (m, 12H); 7.2 (s, 5H), diastereomer H gives N$_\alpha$-(1-S-carbethoxy-3-phenylpropyl)-S-lysyl-1S,2R,4R,6S,7R-tricyclo[5.2.1.0$^{2.6}$]-3-aza-decane-4-carboxylic acid dihydrochloride (diastereomer H′)

$^1$H-NMR (D$_2$O): 0.9–3.0 (m, 18H); 3.0–4.9 (m, 14H); 7.2 (s, 5H), and diastereomer K gives N$_\alpha$-(1-S-carbethoxy-3-phenylpropyl)-S-lysyl-1S,2S,4S,6R,7R-tricyclo[5.2.1.0$^{2.6}$]-3-aza-decane-4-carboxylic acid dihydrochloride (diastereomer K′)

$^1$H-NMR (D$_2$O): 1.0–3.1 (m, 18H); 3.0–4.8 (m, 14H); 7.2 (s, 5H).

EXAMPLE 13

N$_\alpha$-(1-S-Carboxy-3-phenylpropyl)-S-lysyl-1R,2R,4S,6S,7S-tricyclo[5.2.1.0$^{2.6}$]-3-aza-decane-4-carboxylic acid hydrochloride 0.5 g of the ethyl ester dihydrochloride from Example 10d are suspended in 20 ml of dimethoxyethane. Aqueous 4N KOH is added until the pH reaches 9–10. The mixture is stirred for half an hour. It is then adjusted to pH 4 with hydrochloric acid and concentrated to dryness in vacuo, the residue is taken up in ethyl acetate and the mixture is filtered. The ethyl acetate solution is concentrated and the residue is triturated with diisopropyl ether, whereupon it solidifies.

Yield: 300 mg. $^1$H-NMR (D$_2$O): 0.9–2.9 (m, 15H); 3.0–4.9 (m, 12H); 7.2 (s, 5H).

EXAMPLE 14

The following dicarboxylic acids are prepared analogously by the process described in Example 13, starting from the diastereomers E′, F′, G′, H′ and K′:

N$_\alpha$-(1-S-carboxy-3-phenylpropyl)-S-lysyl-1S,2R,4S,6S,7R-tricyclo[5.2.1.0$^{2.6}$]-3-aza-decane-4-carboxylic acid hydrochloride $^1$H-NMR (D$_2$O): 1.0–3.0 (m, 15H), 3.0–5.0 (m, 12H); 7.2 (s, 5H), N$_\alpha$-(1-S-carboxy-3-phenylpropyl)-S-lysyl-1R,2S,4R,6R,7S-tricyclo[5.2.1.0$^{2.6}$]-3-aza-decane-4-carboxylic acid hydrochloride N$_\alpha$-(1-S-carboxy-3-phenylpropyl)-S-lysyl-1R,2S,4S,6R,7S-tricyclo[5.2.1.0$^{2.6}$]-3-aza-decane-4-carboxylic acid hydrochloride $^1$H-NMR (D$_2$O): 1.0–3.3 (m, 16H), 3.3–5.0 (m, 11H), 7.2 (s, 5H)

N$_\alpha$-(1-S-carboxy-3-phenylpropyl)-S-lysyl-1S,2R,4R,6S,7R-tricyclo[5.2.1.0$^{2.6}$]-3-aza-decane-4-carboxylic acid hydrochloride, N$_\alpha$-(1-S-carboxy-3-phenylpropyl)-S-Lysyl-1S,2S,4S,6R,7R-tricyclo[5.2.1.0$^{2.6}$]-3-aza-decane-4-carboxylic acid hydrochloride $^1$H-NMR (D$_2$O): 1.0–3.1 (m, 15H); 3.1–4.9 (m, 12H); 7.2 (s, 5H).

EXAMPLE 15 tert.-Butyl S-alanyl-1R,2R,4S,6S,7S-tricyclo[5.2.1.0$^{2.6}$]-3-aza-decane-4-carboxylate (a) 1:1 mixture of 1R,2R,4S,6S,7S-tricyclo[5.2.1.0$^{2.6}$]-3-aza-decane-4-carboxylate and the corresponding mirror image isomer 2.5 g of the aminoacid from Example 1d are reacted with 30 ml of isobutylene and 2.5 ml of concentrated sulfuric acid in 30 ml of dioxane. After the mixture has been kept at room temperature for 14 hours, it is rendered alkaline with sodium hydroxide solution and concentrated in vacuo, 20 ml of water are added to the residue and the ester is extracted by shaking with methylene chloride. After the methylene chloride has been evaporated off, 2.0 g of colorless oil are obtained.

$^1$H-NMR: 0.9–3.0 (m, 6H); 1.4 (s, 9H); 3.1–4.9 (m, 7H) (after replacement of H by D).

(b) tert.-Butyl N-benzyloxycarbonyl-S-alanyl-1R,2R,4S,6S,7S-tricyclo[5.2.1.0$^{2.6}$]-3-aza-decane-4-carboxylate 0.67 g of 1-hydroxy-benzotriazole and 1.47 g of the tert.-butyl ester prepared in Example 15a are added to a solution of 1 g of Z-Ala-OH in 10 ml of dimethylformamide. The pH vaLue is adjusted to 8.0 with N-ethylmorpholine. The mixture is cooled in an ice-bath, and 1.05 g of dicylohexylcarbodiimide are added. The mixture is stirred at 20°–25° C. for 15 hours. The urea which has precipitated is filtered off with suction, the filtrate is concentrated in vacuo and the residue is taken up in ethyl acetate. The organic phase is washed successively with potassium bisulfate solution, potassium bicarbonate solution and sodium chloride solution, dried and evaporated. The residue is chromatographed on silica gel using ethyl acetate/cyclohexane 1:1 in order to separate the diastereomers.

Yield: 0.7 g of tert.-butyl N-benzyloxycarbonyl-S-alanyl-1R,2R,4S,6S,7S-tricyclo[5.2.0$^{2.6}$]-3-aza-decane-4-carboxylate.

(c) tert.-Butyl S-alanyl-1R,2R,4S,6S,7S-tricyclo[5.2.1.0$^{2.6}$]-3-aza-decane-4-carboxylate 1.2 g of the tert.-butyl ester from Example 15b are dissolved in 20 ml of ethanol and hydrogenation is carried out with 100 mg of Pd/C (10% strength) at room temperature and under normal pressure. The catalyst is filtered off with suction and the residue is concentrated in vacuo.

Yield: 0.8 g of colorless oil. $^1$H-NMR (after replacement of H by D): 0.9–3.1 (m, 6H); 1.2 (d, 3H); 1.4 (s, 9H); 3.1–5.0 (m, 8H).

EXAMPLE 16 tert.-Butyl N-(1-S,R-carbethoxy-3-oxo-3-phenylpropyl)-S-alanyl-1R,2R,4S,6S,7S-tricyclo[5.2.1.0$^{2.6}$]-3-aza-decane-4-carboxylate This compound is prepared from the compound of Example 15b using ethyl benzoylacrylate, analogously to the process described in Example 10a.

EXAMPLE 17

N-(1-S,R-Carbethoxy-3-oxo-3-phenylpropyl)-S-alanyl-1R,2R,4S,6S,7S-tricyclo[5.2.1.0$^{2.6}$]-3-aza-decane-4-carboxylic acid trifluoroacetate 0.5 g of the tert.-butyl ester prepared in Example 16 are dissolved in 5 ml of trifluoroacetic acid and the solution is stirred at room temperature for 30 minutes. The trifluoroacetic acid is then stripped off in vacuo and the residue is triturated with diisopropyl ether.

Yield: 0.25 g of solid residue. $^1$H-NMR (after replacement of H by D): 1.0–3.2 (m, 12H), 3.3–4.9 (m, 13H); 7.2–8.2 (m, 5H).

EXAMPLE 18 tert.-Butyl N-(1-S,R-carbethoxy-3-oxo-3-phenylpropyl)-S-alanyl-1R,2R,4S,6S,7S-tricyclo[5.2.1.0$^{2.6}$]-3-aza-decane-4-carboxylate 5 mmoles of acetophenone, 5 mmoles of ethyl glyoxylate and 5 mmoles of the tert.-butyl ester of Example 14 (c) in 15 ml of glacial acetic acid are heated to 45° C. for 36 hours. After the mixture has been concentrated in vacuo, the residue is rendered neutral with sodium bicarbonate solution and extracted with ethyl acetate. The ethyl acetate phase is concentrated and the residue is chromatographed on silica gel using ethyl acetate/cyclohexane 1:1 as the eluting agent.

EXAMPLE 19 tert.-Butyl N-(1-S-carbethoxy-3-phenylpropyl)-S-alanyl-1R,2R,4S,6S,7S-tricyclo[5.2.1.0$^{2.6}$]-3-aza-decane-4-carboxylate 5 mmoles of the tert.-butyl ester of Example 15c are dissolved in 15 ml of anhydrous ethanol. The solution is adjusted to pH 7.0 with ethanolic potassium hydroxide and 0.7 g of a powdered molecular sieve (4A) and then 5 mmoles of ethyl 2-keto-4-phenyl-butyrate are added thereto. A solution of 0.6 g of sodium cyanoborohydride in 6 ml of anhydrous ethanol is slowly added dropwise. After a reaction time of 20 hours at 20° to 25° C., the solution is filtered and the solvent is distilled off. The residue is taken up in ethyl acetate/water. After the ethyl acetate phases have been evaporated, the residue is chromatographed on silica gel using ethyl acetate/cyclohexane 1:4.

$^1$H-NMR: 1.0–3.0 (m, 16H); 1.4 (s, 9H); 3.0–5.0 (m, 11H); 7.2 (s, 5H) (after replacement of H by D).

EXAMPLE 20

N-(1-S-Carbethoxy-3-phenylpropyl)-S-alanyl-1R,2R,4S,6S,7S-tricyclo[5.2.1.0$^{2.6}$]-3-aza-decane-4-carboxylic acid hydrochloride 0.4 g of the tert.-butyl ester prepared in Example 19 is dissolved in 5 ml of trifluoroacetic acid and the solution is stirred at room temperature for 30 minutes. The trifluoroacetic acid is then stripped off in vacuo. The residue is dissolved in water/methanol and the solution is digested with acetate-charged ion exchanger until the pH is about 5. The ion exchanger is filtered off and the solution is brought to pH 1 with ethanolic hydrochloric acid. The solvent is stripped off in vacuo and the residue is triturated with ether.

Yield: 0.25 g. $R_f$: 0.42 (SiO$_2$; methylene chloride/methanol 8:2).

EXAMPLE 21 tert.-Butyl O-ethyl-S-tyrosinyl-1R,2R,4S,6S,7S-tricyclo[5.2.1.0$^{2.6}$]-3-aza-decane-4-carboxylate (a) tert.-Butyl N-benzyloxycarbonyl-O-ethyl-S-tyrosinyl-1R,2R,4S,6S,7S-tricyclo[5.2.1.0$^{2.6}$]-3-aza-decane-4-carboxylate The compound is prepared from O-ethyl-Z-tyrosine-OH and the tert.-butyl ester described in Example 15a analogously to the process described in Example 15b. The diastereomers are separated over silica gel using cyclohexane/ethyl acetate.

$^1$H-NMR (after replacement of H by D): 0.9–3.0 (m, 11H); 1.4 (s, 9H); 3.0–4.9 (m, 12H); 6.6–7.0 (m, 4H); 7.2 (S, 5H).

(b) tert.-Butyl O-ethyl-S-tyrosinyl-1R,2R,4S,6S,7S-tricyclo[5.2.1.0$^{2.6}$]-3-aza-decane-4-carboxylate (diastereomer 1).

The compound is prepared by hydrogenation of the tert.-butyl ester of Example 21a analogously to Example 15c.

$^1$H-NMR (after replacement of H by D): 1.0–3.1 (m, 11H); 1.3 (s, 9H); 3.1–4.9 (m, 10H); 6.6–7.0 (m, 4H).

The following compounds are obtained from the corresponding starting materials analogously to the process described in Example 21: tert.-butyl O-ethyl-S-tyrosinyl-1S,2S,4S,6R,7R-tricyclo[5.2.1.0$^{2.6}$]-3-aza-decane-4-carboxylate (diastereomer 2), O-ethyl-S-tyrosinyl-1R,2S,4S,6R,7S-tricyclo[5.2.1.0^{2.6}]-3-aza-decane-4-carboxylate (diastereomer 3) and O-ethyl-S-tyrosinyl-1S,2R,4S,6S,7R-tricyclo[5.2.1.0^{2.6}]-3-aza-decane-4-carboxylate (diastereomer 4).

EXAMPLE 22 tert.-Butyl N-(1-S-carbethoxy-3-oxo-3-phenylpropyl)-[O-ethyl-S-tyrosinyl]-1R,2R,4S,6S,7S-tricyclo[5.2.1.0^{2.6}]-3-aza-decane-4-carboxylate (diastereomer 1').

This compound is obtained from the diastereomer 1 from Example 21b and ethyl benzoylacrylate analogously to the process described in Example 10a.

The following compounds are prepared from the diastereomers 2, 3 and 4 analogously to this process: tert.butyl N-(1-S-carbethoxy-3-oxo-3-phenylpropyl)-[O-ethyl-S-tyrosinyl]-1S,2S,4S,6R,7R-tricyclo[5.2.1.0^{2.6}]-3-aza-decane-4-carboxylate (diastereomer 2'), tert.-butyl N-(1-S-carbethoxy-3-oxo-3-phenylpropyl)-[O-ethyl-S-tyrosinyl]-1R,2S,4S,6R,7S-tricyclo[5.2.1.0^{2.6}]-3-aza-decane-4-carboxylate (diastereomer 3') and tert.-butyl N-(1-S-carbethoxy-3-oxo-3-phenylpropyl)-[O-ethyl-S-tyrosinyl]-1S,2R,4S,6S,7R-tricyclo[5.2.2.0^{2.6}]-3-aza-decane-4-carboxylate (diastereomer 4').

EXAMPLE 23

N-(1-S-Carbethoxy-3-oxo-3-phenylpropyl)-[O-ethyl-S-tyrosinyl]-1R,2R,4S,6S,7S-tricyclo[5.2.1.0^{2.6}]-3-aza-decane-4-carboxylic acid trifluoroacetate Diastereomer 1' of Example 22 is reacted by the process described in Example 17.

$^1$H-NMR (after replacement of H by D): 1.0–3.1 (m, 16H); 3.1–4.9 (m, 13H); 6.6–7.0 (m, 4H); 7.2 (s, 5H).

The following compounds are obtained from the diastereomers 2', 3' and 4' analogously to this process: N-(1-S-carbethoxy-3-oxo-3-phenylpropyl)-[O-ethyl-S-tyrosinyl]-1S,2S,4S,6R,7R-tricyclo[5.2.1.0^{2.6}]-3-aza-decane-4-carboxylic acid trifluoroacetate, N-(1-S-carbethoxy-3-oxo-3-phenylpropyl)-[O-ethyl-S-tyrosinyl]-1R,2S,4S,6R,7S-tricyclo[5.2.1.0^{2.6}]-3-aza-decane-4-carboxylic acid trifluoroacetate and N-(1-S-carbethoxy-3-oxo-3-phenylpropyl)-[O-ethyl-S-tyrosinyl]-1S,2R,4S,6S,7R-tricyclo[5.2.1.0^{2.6}]-3-aza-decane-4-carboxylic acid trifluoroacetate.

EXAMPLE 24 tert.-Butyl N-(1-S-carbethoxy-3-phenylpropyl)-[O-ethyl-S-tyrosinyl]-1R,2R,4S,6S,7S-tricyclo[5.2.1.0^{2.6}]-3-aza-decane-4-carboxylate (diastereomer 1)

This compound is obtained from the compound of Example 21b and ethyl 2-keto-4-phenyl-butyrate analogously to the process described in Example 19.

$^1$H-NMR (after replacement of H by D): 1.0–3.0 (m, 18H); 1.4 (s, 9H); 3.1–5.0 (m, 13H); 6.6–7.0 (m, 4H); 7.2 (s, 5H).

The following compounds are obtained from the diastereomers 2, 3 and 4 of Example 21 and ethyl 2-keto-4-phenyl-butyrate analogously to this process: tert.-butyl N-(1-S-carbethoxy-3-phenylpropyl)-[O-ethyl-S-tyrosinyl]-1S,2S,4S,6R,7R-tricyclo[5.2.1.0^{2.6}]-3-aza-decane-4-carboxylate (diastereomer 2); $^1$H-NMR (after replacement of H by D): 1.0–3.0 (m, 18H); 1.4 (s, 9H); 3.0–4.9 (m, 13H); 6.6–7.0 (m, 4H); 7.2 (s, 5H), tert.-butyl N-(1-S-carbethoxy-3-phenylpropyl)-[O-ethyl-S-tyrosinyl]-1R,2S,4S,6R,7S-tricyclo[5.2.1.0^{2.6}]-3-aza-decane-4-carboxylate (diastereomer 3); $^1$H-NMR (after replacement of H by D): 1.0–3.0 (m, 18H); 1.4 (s, 9H); 3.0–5.0 (m, 13H); 6.6–7.0 (m, 4H); 7.2 (s, 5H) and tert.-butyl N-(1-S-carbethoxy-3-phenylpropyl)-[O-ethyl-S-tyrosinyl]-1S,2R,4S,6S,7R-tricyclo[5.2.1.0^{2.6}]-3-aza-decane-4-carboxylate (diastereomer 4); $^1$H-NMR (after replacement of H by D): 0.9–3.1 (m, 18H); 1.4 (s, 9H); 3.2–4.9 (m, 13H); 6.6–7.0 (m, 4H); 7.2 (s, 5H).

EXAMPLE 25

N-(1-S-Carbethoxy-3-phenylpropyl)-[O-ethyl-S-tyrosinyl]-1R,2R,4S,6S,7S-tricyclo[5.2.1.0^{2.6}]-3-aza-decane-4-carboxylic acid hydrochloride The carboxylic acid is obtained by reacting the tert.-butyl ester of Example 24 with trifluoroacetic acid analogously to the process described in Example 20.

$^1$H-NMR (after replacement of H by D): 1.0–3.1 (s, 18H); 3.1–5.0 (m, 13H); 6.6–7.0 (m, 4H); 7.2 (s, 5H).

The following compounds are obtained analogously from the diastereomers 2, 3 and 4 of Example 24: N-(1-S-carbethoxy-3-phenylpropyl)-[O-ethyl-S-tyrosinyl]-1S,2S, 4S,6R,7R-tricyclo[5.2.1.0^{2.6}]-3-aza-decane-4-carboxylic hydrochloride; $^1$H-NMR (after replacement of H by D): 0.9–3.0 (m, 18H), 3.0–4.9 (m, 13H); 6.6–7.0 (m, 4H); 7.2 (s, 5H), N-(1-S-carbethoxy-3-phenylpropyl)-[O-ethyl-S-tyrosinyl]-1R,2S,4S,6R,7S-tricyclo[5.2.1.0^{2.6}]-3-aza-decane-4-carboxylic acid hydrochloride; $^1$H-NMR (after replacement of H by D): 1.0–2.9 (m, 18H); 3.0–4.9 (m, 13H); 6.6–7.0 (m, 4H); 7.2 (s, 5H) and N-(1-S-carbethoxy-3-phenylpropyl)-[O-ethyl-S-tyrosinyl]-1S,2R,4S,6S,7R-tricyclo[5.2.1.0^{2.6}]-3-aza-decane-4-carboxylic acid hydrochloride; $^1$H-NMR (after replacement of H by D): 1.0–3.1 (m, 18H); 3.1–5.0 (m, 13H); 6.6–7.0 (m, 4H); 7.2 (s, 5H).

We claim:
1. A compound of the formula I

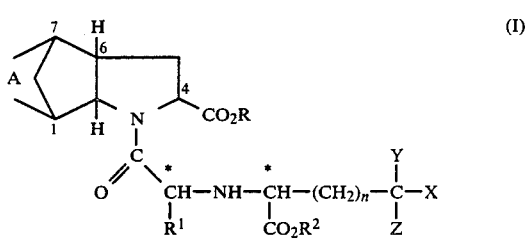

in which
n denotes 0 or 1;
A denotes —CH=CH— or —CH$_2$—CH$_2$—;
R denotes hydrogen; (C$_1$ to C$_6$)-alkyl or aralkyl with 7 to 9 carbon atoms;
R$^1$ denotes hydrogen;
(C$_1$ to C$_6$)-alkyl; or
a side chain of a naturally occurring aminoacid selected from the group consisting of Ser, Thr, Asp, Asn, Glu, Gln, Arg, Lys, Hyl, Cys, Orn, Cit, Tyr, Trp, His, Hyp and Ala; or a side chain of said naturally occurring amino acid protected by a protective group;
R$^2$ denotes hydrogen; (C$_1$ to C$_6$)-alkyl; (C$_2$ to C$_6$)-alkenyl; or (C$_6$ to C$_{12}$)-aryl-(C$_1$ to C$_4$)-alkyl;
Y denotes hydrogen or hydroxyl; and
Z denotes hydrogen; or
Y and Z together denote oxygen; and X denotes ($C_1$ to $C_6$)-alkyl; ($C_2$ to $C_6$)-alkenyl; ($C_5$ to $C_9$)-cycloalkyl; or ($C_6$ to $C_{12}$)-aryl; or such ($C_6$ to $C_{12}$)-aryl mono-, di- or tri-substituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkylamino and/or methylenedioxy; or 3-indolyl; or a physiologically acceptable salt thereof.

2. A compound of the formula I as claimed in claim 1, in which the hydrogen atoms on the bridg head C-2 C-6 are in the cis-configuration relative to one another, the pyrrolidine ring on C-2 and C-6 is orientated in the endo- or exo-position relative to the bicyclic radical and the —$CO_2R$ group on C-4 is orientated in the cis- or trans-position relative to the H atom on C-2.

3. A compound of the formula I as claimed in claim 1, in which the carbon atom in position 4 in the formula I and the carbon atoms labeled with an asterisk in the side chain each have the S-configuration.

4. A compound of the formula I as claimed in claim 1, in which n denotes 1;
A denotes $CH_2$—$CH_2$;
R denotes hydrogen or ($C_1$ to $C_4$)-alkyl;
$R^1$ denotes hydrogen; ($C_1$ to $C_3$)-alkyl; or a side chain of a naturally occurring aminoacid selected from the group consisting of Ser, Thr, Asp, Asn, Glu, Gln, Arg, Lys, Hyl, Cys, Orn, Cit, Tyr, Trp, His, Hyp and Ala; or a side chain of said naturally occurring amino acid protected by a protective group;
$R^2$ denotes hydrogen; ($C_1$ to $C_4$)-alkyl; or benzyl; X denotes phenyl, which can be mono- or di-substituted by ($C_1$ or $C_2$)-alkyl, ($C_1$ or $C_2$)-alkoxy, hydroxyl, fluorine, chlorine, bromine, amino, ($C_1$ to $C_4$)-alkylamino, di-($C_1$ to $C_4$)-alkylamino, nitro and/or methylenedioxy; or trisubstituted by methoxy.

5. A compound of the formula I as claimed in claim 1, in which R denotes hydrogen, $R^1$ denotes methyl and X denotes phenyl.

6. A compound of the formula I as claimed in claim 1, in which R denotes hydrogen, $R^1$ denotes methyl, X denotes phenyl and $R^2$ denotes hydrogen or ethyl.

7. A compound of the formula I as claimed in claim 1, in which the carboxyl group on the carbon atom in position 4 of the formula I is orientated in the cis- or trans-position relative to the H atom on C-2, the pyrrolidine ring is orientated in the exo- or endo-position relative to the bicyclic radical, C-4 in the formula I and the carbon atoms labeled with an asterisk in the side chain each have the S-configuration, n denotes 1,
A denotes $CH_2$-$CH_2$,
R denotes hydrogen,
$R^1$ denotes methyl,
$R^2$ denotes ethyl,
Y and Z each denote hydrogen and
X denotes phenyl.

8. A pharmaceutical composition comprising an effective amount of a compound of the formula I or a mixture of compounds according to claim 1 or a physiologically tolerable salt thereof and a physiologically tolerable carrier.

9. A method of treating hypertension by administering an effective amount of a compound of the formula I according to claim 1 or a physiologically tolerable salt thereof.

10. A compound of formula I as claimed in claim 1 in which $R^1$ denotes a side chain of a naturally occurring amino acid selected from the group consisting of Ser, Thr, Asp, Asn, Glu, Gln, Arg, Lys, Hyl, Cys, Orn, Cit, Tyr, Trp, His, Hyp and Ala; or a side chain of said naturally occurring amino acid protected by a protective group.

* * * * *